May 14, 1940. M. OKADA Plant Pat. 398
PINK CARNATION
Filed May 22, 1939
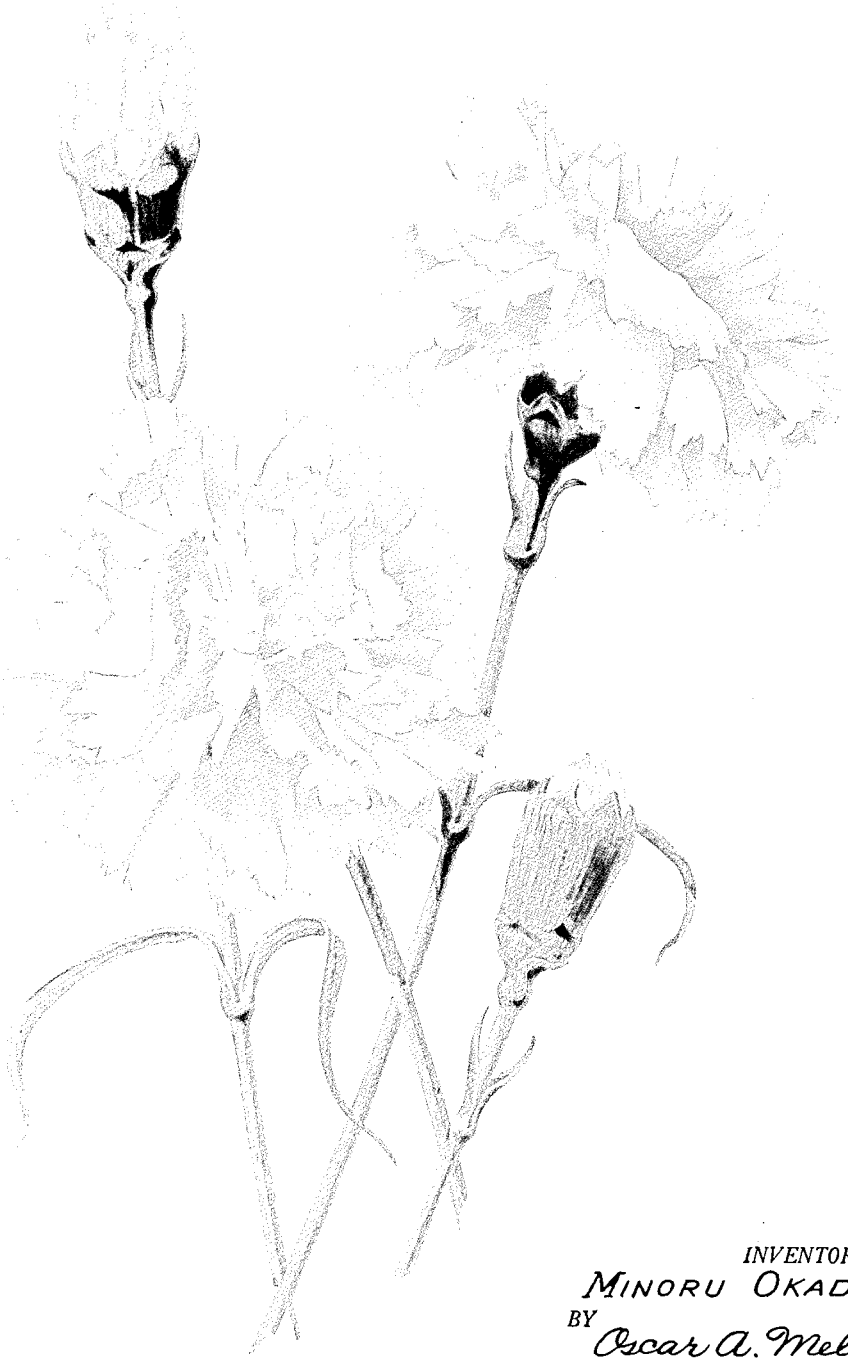
INVENTOR.
MINORU OKADA
BY Oscar A. Mellin
ATTORNEY.

Patented May 14, 1940

Plant Pat. 398

UNITED STATES PATENT OFFICE

398

PINK CARNATION

Minoru Okada, San Lorenzo, Calif.

Application May 22, 1939, Serial No. 275,028

1 Claim. (Cl. 47—60)

This invention relates generally to carnations of the greenhouse forcing type and particularly pertains to a carnation of a novel color and extraordinary size.

The outstanding characteristics of my new variety of carnation are the distinctive color of the blossom, the large size, and the fullness and highness of the center of the blossom.

I originated this new variety by crossing carnation "Pink Spectrum" with "Pink Abundant," neither of which has the distinct and different color of my new variety. The carnation "Pink Abundant" is the seed bearing parent.

My new variety has been asexually reproduced over a period of approximately two years and its distinctive color and size have persisted without change.

The new variety of carnation is illustrated in natural size and in approximately natural color in the original drawing, which includes a side and a front view of an open blossom and views of partly open buds. I desire to point out here that some allowance must be made for the coloring of the drawing, due to the impossibility of the artist to obtain the exact color of the natural blossom or the uniformity thereof. However, I hereinafter refer to Ridgway's "Color Standards and Color Nomenclature" in order to point out as exactly as possible the color of the blossom.

The color of the blossom is extremely close to that labeled Thulite Pink in Ridgway's "Color Standards and Color Nomenclature." It should be pointed out, however, that some of the petals of the plant, when in full bloom, show a few vein-like lines of a darker shade of pink which (as in the case of the exact color) it is impossible for the artist to reproduce on the accompanying drawing.

The plant itself is a vigorous one with very stiff stems from 36 to 42 inches long. The leaves are (at the base of the stems) approximately ⅜ of an inch wide to $\frac{9}{16}$ of an inch wide at the upper end of the stem with a medium curl. The length of the leaves at the base of the stem is usually between five and six inches long, which leaves, of course, considerably reduce in length on the stem toward the blossom end. The leaves are inclined to be rather upright, although some of them noticeably curl slightly. The stem is deep dull yellow green in color changing to dark yellow green in color from one node to the next above succeeding node covered with a grayish bloom. The color of the stem corresponds approximately to the color Deep Dull Yellow Green #1 and Dark Dull Yellow Green, set out on Plate #XXXII in Ridgway's "Color Standards and Color Nomenclature." The leaves are of a deep green corresponding to Empire Green, set out in Ridgway's "Color Standards and Color Nomenclature," Plate #XXXII.

The buds are somewhat thick relative to their length and are rather blunt as illustrated. The blossom is unusually large with a diameter between 3½ inches and 4 inches, with approximately 50 petals which are rather full with serrated edges and very gently ruffled. The center of the blossom is high with curled petals projecting somewhat coaxially from the calyx.

The calyx is a five lobed tube which does not split and which is of a green color corresponding to Dark Yellow Green, set out on Plate XXXII in Ridgway's "Color Standards and Color Nomenclature." The calyx is approximately 1 inch long, $\frac{9}{16}$ of an inch in diameter at the smaller end and ⅞ of an inch in diameter at the larger end.

The ovary is hard and is approximately ½ of an inch long with two and sometimes three and sometimes four styles about 1 inch long with curled ends projecting from the top. These styles project from the very top and center of the ovary with their bases close together arranged circular fashion around the top of the ovary, the outer ends of the styles terminating in usually two stigmas. The styles are white with a slight greenish tinge, there being no color chart in Ridgway's "Color Standards and Color Nomenclature" closely corresponding to the color of these styles and stigmas. The ovary arises from a short pithy cup and the stamens arise from this cup at the outer circumference of the ovary. The entire length of the pistil is about 1¾ inches. The color of the filaments of the stamens is white and the anthers are white turning to a slight cream color at the top, but there is no color chart in Ridgway's "Color Standards and Color Nomenclature" closely corresponding to this color.

The blossom has a rather mild fragrance.

Having thus described my invention, what I claim and desire to secure by Letters Patent is:

A new variety of carnation substantially as illustrated and described characterized particularly by the distinctive color and large size of the blossom as illustrated and described, and the high center of its blossom when in full bloom.

MINORU OKADA.